United States Patent [19]
McWha

[11] Patent Number: 5,871,470
[45] Date of Patent: Feb. 16, 1999

[54] COMBINED SPINAL EPIDURAL NEEDLE SET

[75] Inventor: Keith J. McWha, Waldwick, N.J.

[73] Assignee: Becton Dickinson and Company, Franklin Lakes, N.J.

[21] Appl. No.: 844,283

[22] Filed: Apr. 18, 1997

[51] Int. Cl.$^6$ .................................................. A61M 5/178
[52] U.S. Cl. .......................... 604/158; 604/164; 604/272
[58] Field of Search .................................... 604/158, 164, 604/165, 272, 274

[56] References Cited

U.S. PATENT DOCUMENTS

| | | | |
|---|---|---|---|
| 5,085,631 | 2/1992 | Leighton | 604/28 |
| 5,480,389 | 1/1996 | McWha et al. | 604/165 |
| 5,527,290 | 6/1996 | Zadini et al. | 604/165 |
| 5,573,519 | 11/1996 | Zohmann | 604/272 |
| 5,584,820 | 12/1996 | Gurmarnik | 604/264 |

*Primary Examiner*—Wynn Wood Coggins
*Assistant Examiner*—Cris L. Rodriguez
*Attorney, Agent, or Firm*—Arthur D. Dawson

[57] ABSTRACT

A combined spinal epidural needle set of the present invention includes an epidural needle with an overall length, an open distal end and a proximal end with a hub. The epidural needle has a hollow bore therethrough having an inside diameter. The set of the invention includes a spinal needle with an overall length greater than the length of the epidural needle, a pointed distal end, a proximal end with a hub and a hollow passage therethrough. The spinal needle has an outside diameter less than the inside diameter of the bore of the epidural needle. The spinal needle is slidably disposed for movement within the epidural needle between a position wherein the distal point of the spinal needle is substantially coincident with the open distal end of the epidural needle and at least one position wherein the distal point of the spinal needle projects beyond the open distal end of the epidural needle. The hubs of the epidural needle and the spinal needle each include an adjustable engagement for preselecting the position of the distal point of the spinal needle with respect to the open distal end of the epidural needle.

20 Claims, 13 Drawing Sheets

COMBINED SPINAL EPIDURAL NEEDLE SET

FIELD OF INVENTION

The present invention is generally related to the field of hypodermic needles and more specifically to hypodermic needles intended for administration and withdrawal of fluids to the spine of a patient.

BACKGROUND

Generally speaking, there are two basic techniques for introducing injectable medicament into the spinal area of a patient. The techniques both can be used to create spinal anesthesia, one being delivery of the medicament into the epidural space, "epidural," and the other, penetration of the dural membrane with delivery of the medicament into the subarachnoid space, "spinal" or "subarachnoid." The medicaments can be any type of liquid therapeutic material including antibiotics, steroids and the like, but generally are agents used for anesthesia and analgesia. When the liquid medicament is an anesthetic agent, a subarachnoid placement is recognized as providing a faster, more uniform distribution, but several major side effects may result from an improper subarachnoid placement. These side effects may include nerve damage, either from contact with the needle or from high local concentrations of the medicament, pooling or inadequate mixing of the medicament in the cerebrospinal fluid.

Delivery of the medicament into the subarachnoid space requires a penetration depth of several centimeters. Puncture of the dural membrane for introduction of a needle or catheter with a large gauge needle may result in postoperative leakage of cerebrospinal fluid from the puncture site, often resulting in severe postoperative headaches. Thus, when puncture of the dural membrane is made with a needle, the smaller the size of the puncture the lower the probability of post-procedural leakage of cerebrospinal fluid. Small diameter needles of the length required to enter the subarachnoid space are quite flexible and as a result, difficult to accurately position when making penetrations to a depth of several centimeters. Practitioners have recognized the need to use a needle with sufficient stiffness to make the initial penetration and the need to use a small diameter needle for penetration of the dural membrane. This recognition has evolved into the use of an eight to ten centimeters long, larger diameter (ca. 16–18 gauge) introducer needle to enter the epidural space followed by the use of the bore of the introducer needle to place a longer, i.e., twelve to sixteen centimeters long, smaller diameter (ca. 22–28 gauge) spinal needle adjacent to and then to penetrate the dural membrane. The spinal needle is then used to administer a bolus of the anesthetic agent. The bolus results in rapid onset of anesthesia, and depending upon the placement and the amount administered, the effect may last several hours.

Correct placement and delivery of a subarachnoid inedicament is recognized by practitioners as being one of the more technique sensitive procedures currently practiced. There is considerable anatomical variation between patients related to the patient's size and weight. The practitioner generally positions the introducer needle between the vertebrae into the epidural space against the dural membrane, then advances the spinal needle through the dura into the subarachnoid space. Accurately perceiving when the dura has been penetrated is often difficult for the practitioner. There are several widely practiced techniques to confirm that the needle has entered the subarachnoid space. Some practitioners depend upon feeling a "pop" as the spinal needle penetrates the dura. Other practitioners routinely place a drop of fluid on the proximal hub of the spinal needle and depend upon observing the drop being drawn into the hub when the dura is penetrated. Many practitioners also often confirm that the subarachnoid space is penetrated by using the spinal needle to withdraw a sample of cerebrospinal fluid.

A survey of previous patent literature reports in this general area is found in U.S. Pat. No. 5,085,631. The patent discloses a method for placement of a subarachnoid catheter that utilizes a three component apparatus comprising an outer needle, an inner needle and a catheter intermediate the two needles.

A recent U.S. Pat. No. 5,480,389, discloses a regulating device for adjusting the length of a combined spinal epidural needle and the method of practicing its use. The disclosed invention utilizes standard commercially available spinal and epidural needles, providing a fixture for preselecting the spinal needle projection with respect to the epidural needle when the spinal needle is coaxially placed within the epidural needle. While this regulating device and method is quite useful in the practice of combine spinal epidural medication, the use of this device adds an additional item to the procedure kit, and additional manipulations.

Another recent U.S. Pat. No. 5,584,820, discloses a set for spinal anesthesia that has a hollow introducer needle, a spinal needle introducible through the introducer needle into the subarachnoid space, a stylet extendable through the spinal needle and an enlongate hollow sleeve. The disclosed hollow sleeve has a first hollow portion extending into the interior of the introducer needle and a second hollow portion extending longitudinally from the first hollow portion over the spinal needle only. The hollow sleeve is provided with a perpendicular screw disposed to be advanced against the cannula of the spinal needle to retain the spinal needle in a fixed position with respect to the introducer needle. The impingement of the perpendicular retaining screw directly upon the cannula of the spinal needle may result in particulate generation or damage to the small diameter spinal needle. Additionally, a gloved practitioner may have difficulty manipulating the necessarily small retention screw while holding the needles at the desired position.

Subarachnoid placement of medicaments, if done properly, is acknowledged to be desirable. Thus, a device and a method for its use that would minimize the size of the puncture of the dural membrane, allow accurate and controlled placement of a therapeutically effective amount of a medicament within the subarachnoid space, thereby reducing the potential for nerve damage, coupled with an ability to rapidly initiate and maintain a therapeutic level of the medicament for longer procedures would represent an advance to the medical arts. A method and apparatus that addresses these needs constitute the present invention.

SUMMARY

A combined spinal epidural needle set of the present invention includes an epidural needle with an overall length, an open distal end and a proximal end with a hub. The epidural needle has a hollow bore therethrough having an inside diameter. The set of the invention includes a spinal needle with an overall length greater than the length of the epidural needle, a pointed distal end, a proximal with a hub and a hollow passage therethrough. The spinal needle has an outside diameter less than the inside diameter of the bore of the epidural needle. The spinal needle is slidably disposed for movement within the epidural needle between a position wherein the distal point of the spinal needle is substantially coincident with the open distal end of the epidural needle and at least one position wherein the distal point of the spinal needle projects a distance beyond the open distal end of the epidural needle. The hubs of the epidural needle and the spinal needle each include an adjustable engagement for preselecting and releasably maintaining the position of the distal point of the spinal needle with respect to the open distal end of the epidural needle.

The invention allows a practitioner to position the needle set, with the point of the spinal needle substantially coincident with the point of the epidural needle, within the epidural space so that the distal point of the epidural needle is adjacent the dura. The practitioner then advances the spinal needle a preselected distance beyond the distal point of the epidural needle, advances the needle set so that the projecting point of the spinal needle penetrates the dura and then may confirm the placement of the spinal needle in the subarachnoid space with the presence of cerebrospinal fluid at the hub of the spinal needle. The use of the needle set of the invention substantially eliminates uncertainty of the placement of the spinal needle in the subarachnoid space by providing the practitioner with a preselected projection of the spinal needle beyond the open distal end of the epidural needle.

DETAILED DESCRIPTION

While this invention is satisfied by embodiments in many different forms, there is shown in the drawings and herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents. For the purposes of this description of the present invention, the term "distal end" refers to the end of the assembly closest to the needle point and the patient, whereas the term "proximal end" refers to the end of the assembly furthest from the needle point and closest to the practitioner.

Figure 1:
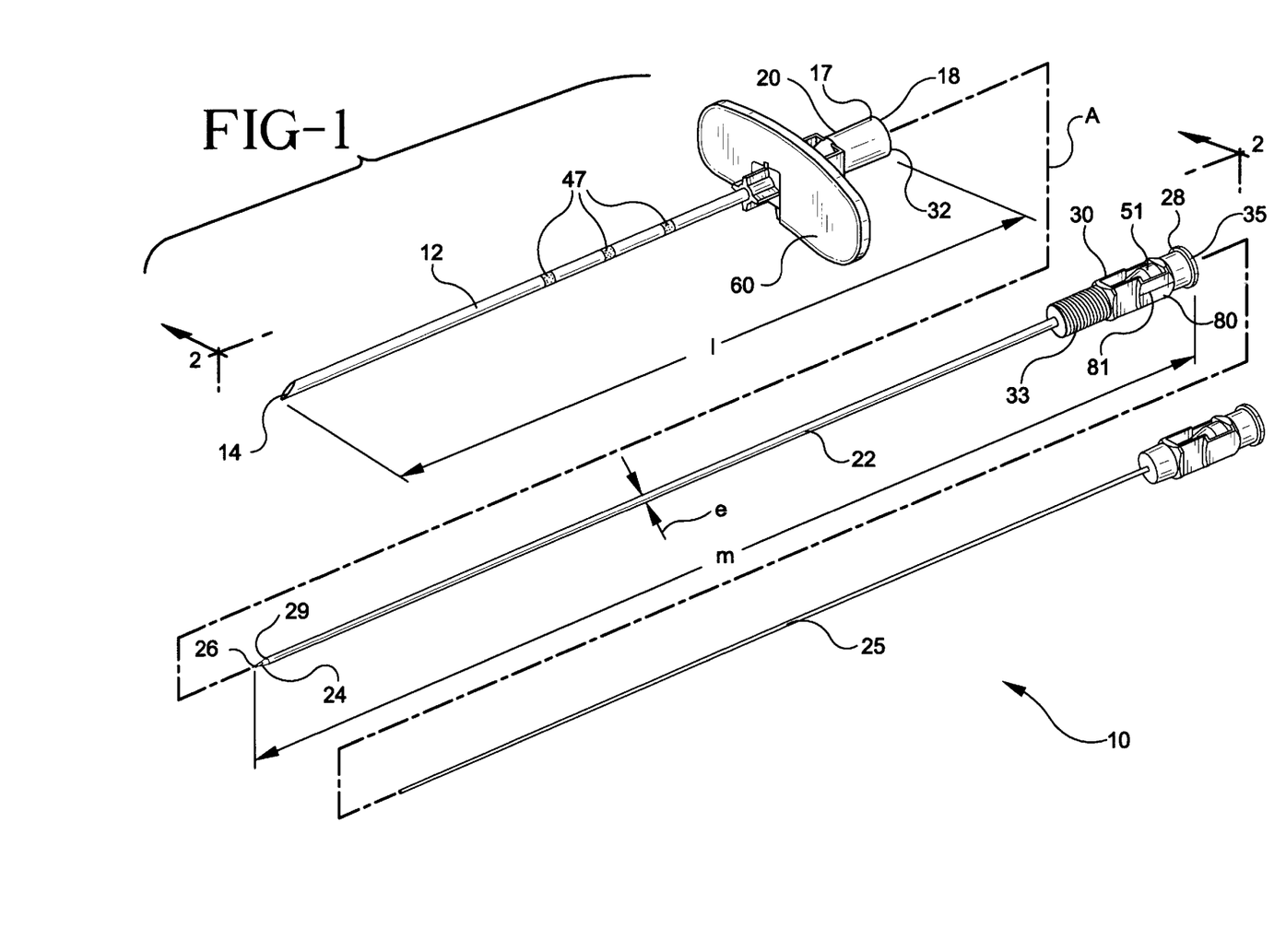
FIG. 1 is an exploded perspective view of the combined spinal epidural needle set of the invention.
Figure 2:
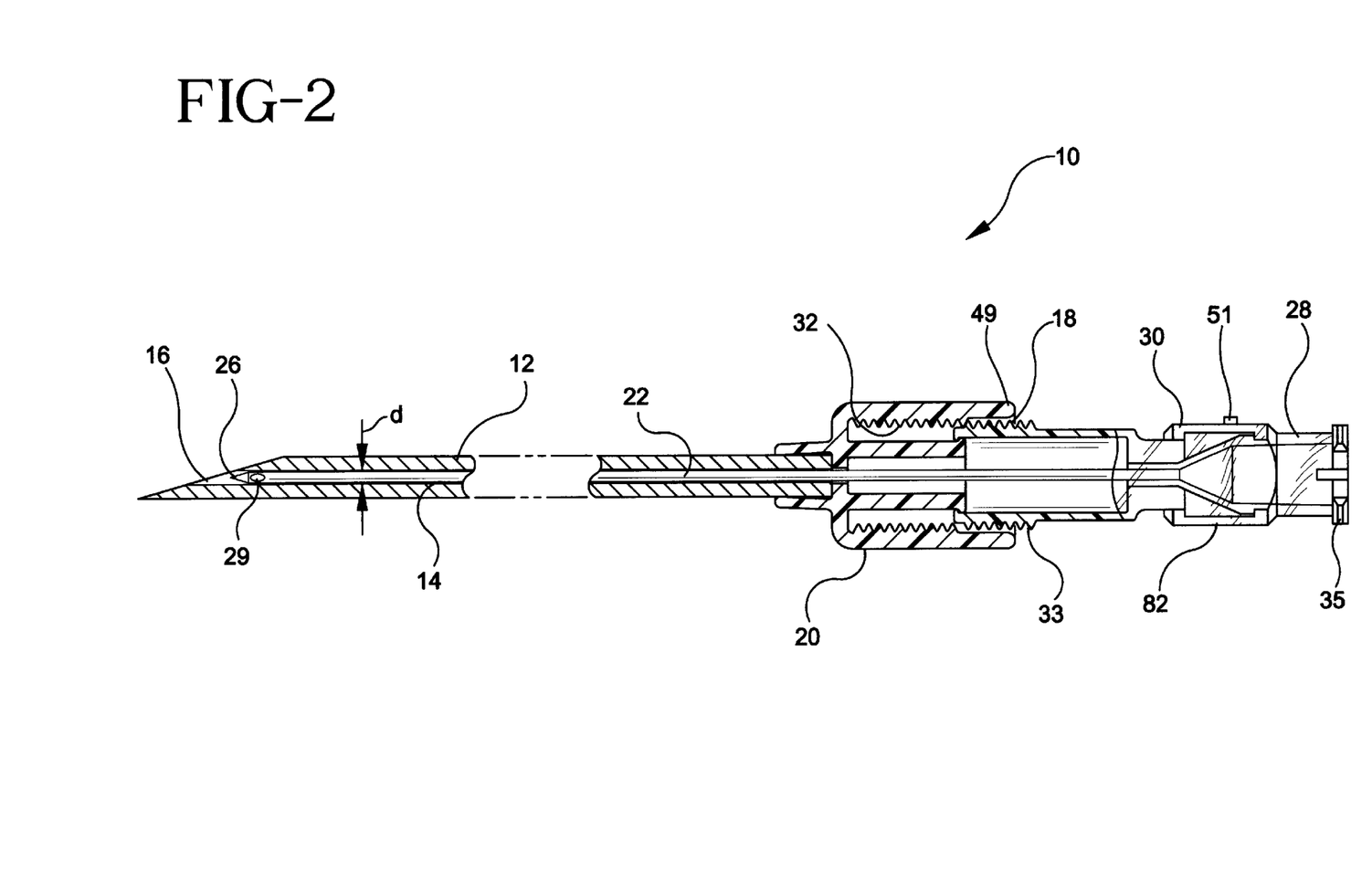
FIG. 2 is a cross-sectional view of the needle set of FIG. 1 taken along the line 2—2.
Figure 3:
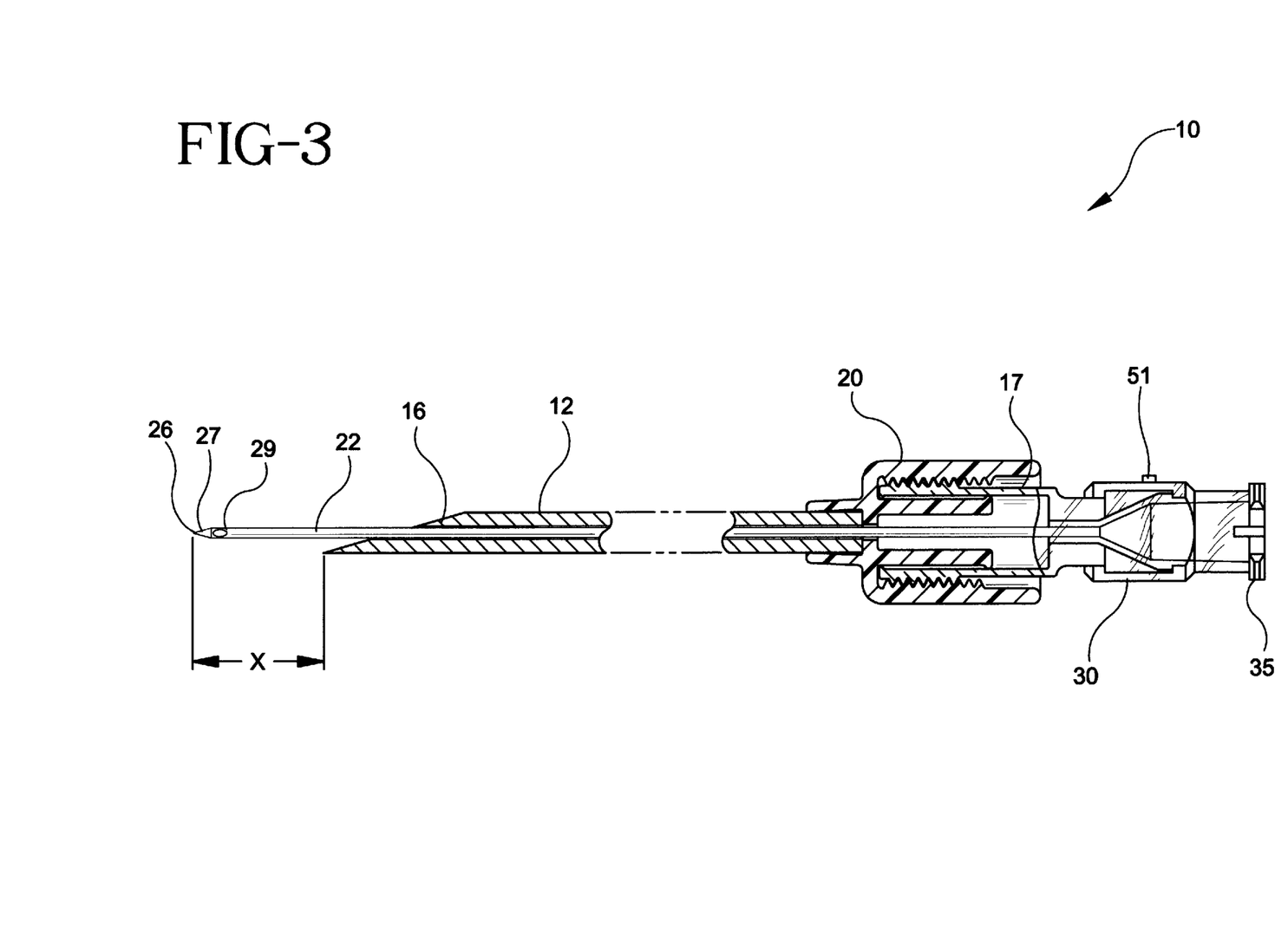
FIG. 3 is a cross-sectional view of the needle set of FIG. 1, analogous to FIG. 2 with the spinal needle projecting from the epidural needle.

Referring to FIGS. 1–6, a combined spinal epidural needle set 10 includes an epidural needle 12 with an overall length "l", a hollow bore 14 defining an axis "A" therethrough having an inside diameter "d". Needle 12 has an open distal end 16, a proximal end 18 and includes a hub 20. Needle set 10 includes a spinal needle 22 with an overall length "m" greater than length "l" of epidural needle 12. Spinal needle 22 has an outside diameter "e" less than said inside diameter "d" of bore 14 of epidural needle 12. Spinal needle 22 has a hollow passage 24 therethrough, a pointed distal end 26, preferably a "pencil point" 27, with at least one, preferably two, diametrically opposed side port openings 29, a proximal end 28 and includes a hub 30. As shown in FIG. 2, spinal needle 22 is slidably disposed for movement within bore 14 of epidural needle 12 between a position where distal point 26 of the spinal needle is substantially coincident with open distal end 16 of epidural needle 12 and at least one position, as shown in FIG. 3, wherein distal point 26 of the spinal needle projects a distance "x" beyond open distal end 16 of epidural needle 12.

Epidural needle hub 20 and spinal needle hub 30 include conjugate threads 32 and 33 respectively, so that the projection distance "x" of distal point 26 of the spinal needle with respect to open distal end 16 of the epidural needle may be adjusted by rotation of the spinal needle hub with respect to the epidural needle hub. The rotation of the spinal needle hub with respect to the epidural needle hub, thereby advances or retracts distal point 26 of the spinal needle. Preferably, threads 32 on epidural needle hub 20 are female threads and threads 33 on spinal needle hub 30 are male threads. The movement of distal point 26 of the spinal needle with respect to open distal end 16, the projection distance "x", of the epidural needle is preferably a distance between about a position wherein the distal ends of the spinal and the epidural needle are substantially coincident (best seen in FIG. 2) and a position wherein of distal point 26 of the spinal needle projects about 18 mm beyond open distal end 16 (best seen in FIG. 3). Preferably, hub 20 of epidural needle 12 also includes a removable finger press structure 60 to assist the practitioner in placement and advancement of epidural needle into the patient's spine. Additionally, both hub 20 of the epidural needle and hub 30 of the spinal needle preferably each include a female luer fitting 17 and 35, respectively, for attachment of a fluid handling device.

Figure 4:
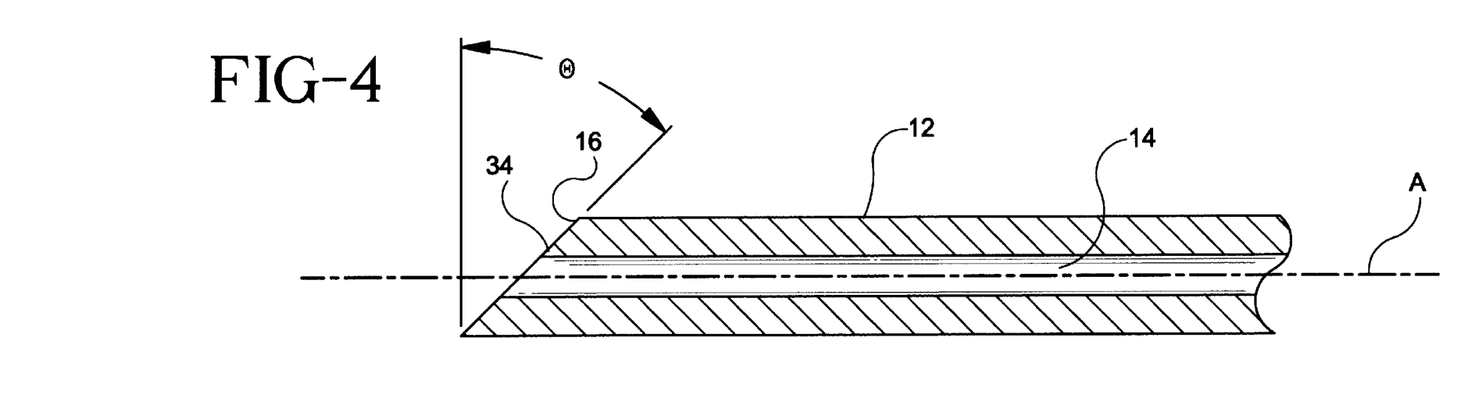
FIG. 4 is a cross-sectional view of the distal tip region of a "Crawford" type epidural needle.
Figure 4A:
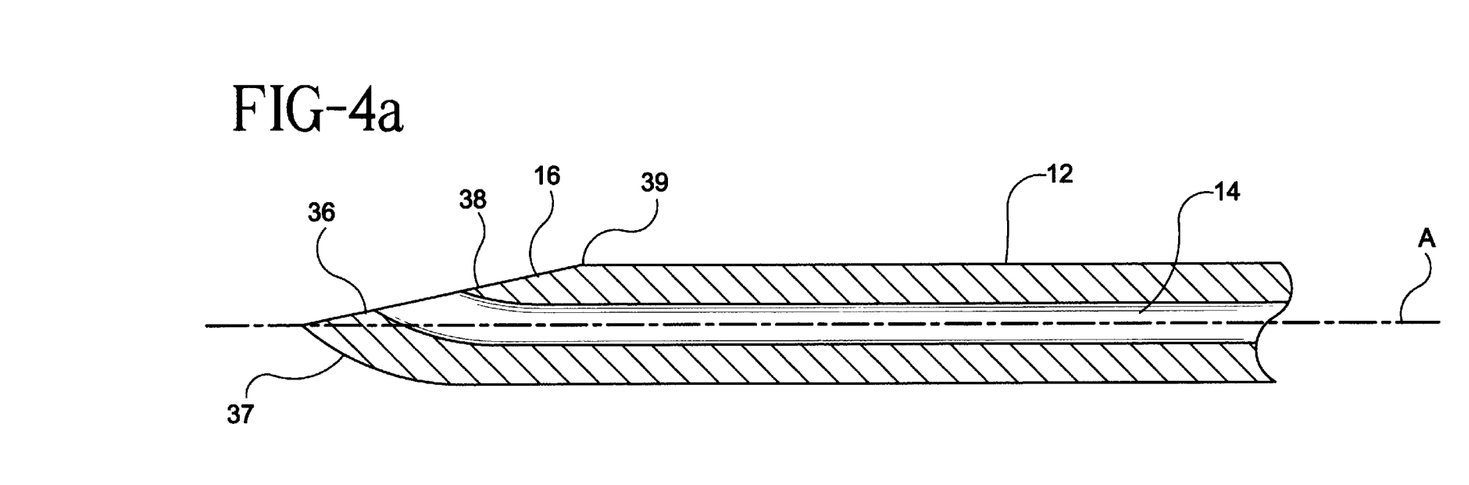
FIG. 4a is a cross-section view of the distal tip region of a "Tuohy" type epidural needle.

Referring to FIGS. 4 and 4a, open distal end 16 of epidural needle 12 preferably is either one of these two configurations. FIG. 4 illustrates open distal end 16 with a "Crawford" type point that has a bevel 34 at θ=45° across axis A with the axis as the center line of the opening. FIG. 4a illustrates open distal end 16 with "Touhy" type point 36. The "Tuohy" type point is formed by a gentle bend 37 of needle 12 away from axis A and a bevel 38 extending from axis A to the tubing edge 39. Both of the preferred configurations are well accepted for epidural needles, and individual practitioners generally prefer one or the other.

Figure 5:
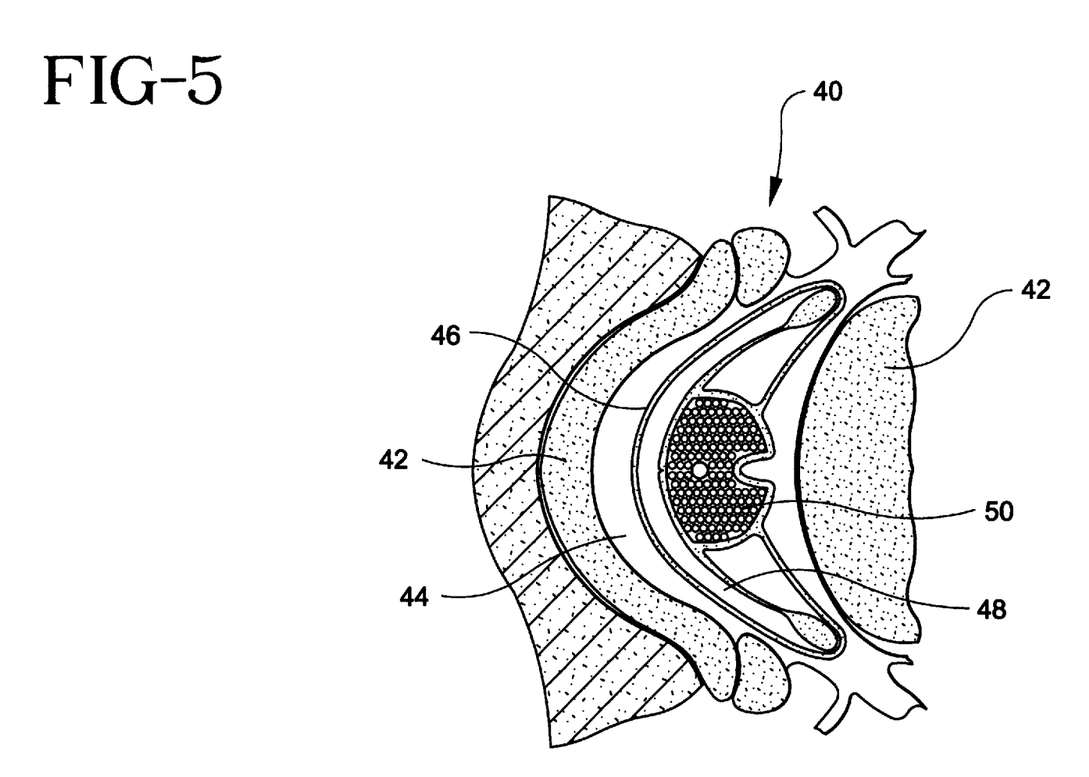
FIG. 5 is a schematic horizontal cross-sectional view of the human spine.
Figure 6:
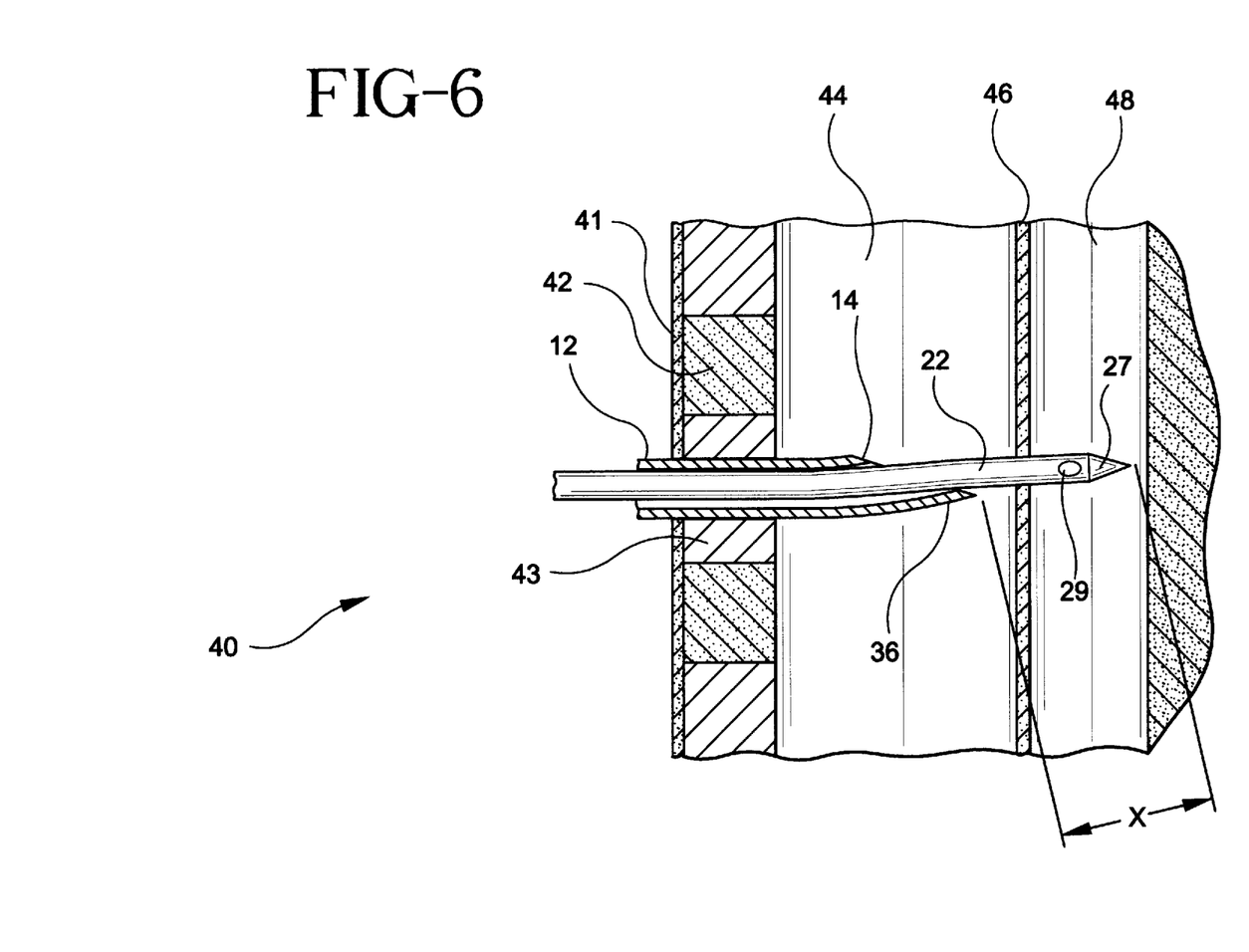
FIG. 6 is a schematic vertical cross-sectional view of the human spine with the invention of FIG. 1 positioned for administration of a medicament.

FIG. 5 schematically illustrates a horizontal cross sectional view of a human spine 40. This illustration, of the lower portion of spine 40, includes bone 42, epidural space 44, dural membrane 46, subarachnoid space 48 and the caunda equina ("horses tail"—In this region, the spinal cord separates into a bundle of individual nerves.) region 50 of the spinal cord. Referring now to FIG. 6, a schematic vertical cross section of spine 40 is illustrated. In the placement of spinal needle 22 to deliver a medicament into subarachnoid space 48, epidural needle 12, with distal point 26 of spinal needle 22 substantially coincident with open distal end 16 of the epidural needle, is advanced into epidural space 44 through skin 41 and ligamentous tissue 43 between bony segments 42 of the spine so that open distal end 16 of the epidural needle is adjacent to dural membrane 46. Spinal needle 22 is then advanced so that point 26 projects distance "x" beyond open distal end 16 of the epidural needle. Pencil point configuration 27 is preferred for the spinal needle since this point configuration tends to spread the fibers of the dura rather than cutting. The spreading tendency of the pencil point has two benefits. The size of the puncture opening in the dura is minimized, thus substantially reducing the occurrence of post-operative cerebrospinal fluid leakage that is believed to cause post-operative "spinal" headaches. Additionally, should spinal needle 22 come into contact with one of the branching nerves from spinal cord bundle, pencil point 27 is less likely to damage the nerve than a "cutting" bevel configuration of a standard hypodermic needle. In this illustrated example, open distal end 16 has the "Touhy" point configuration, other point configurations, including, but not limited to the "Crawford" configuration are also suitable and are considered to be within the scope of the invention. When the assembly with spinal needle 22 projected the preselected distance beyond open distal end 16 of the epidural needle is advanced distally, distal point 26 of the spinal needle penetrates dural membrane 46 and projects into subarachnoid space 48 a sufficient distance to ensure that the preferred side port 29 is within the subarachnoid space. This projection allows the practitioner to confirm the placement by the presence of cerebrospinal fluid then administer the medicament. Since the distance "x" of the projection is adjustable by the practitioner, a projection distance "x" may be preselected with consideration of the patients physical size or other anatomical variations. Preferably, epidural needle 12 includes a plurality of graduated depth markings 47 to assist the practitioner in determining the correct placement of the epidural needle. Both epidural needle hub 20 and spinal needle hub 30, either separately or in combination with each other, preferably include an indication 49 of projection distance "x" of spinal needle distal point 26 from the epidural needle distal end 16. Indication 49 may be provided simply by the amount of exposed threads 33, observation of spinal needle hub 30 through a transparent epidural needle hub 20 or by discrete markings. Additionally, when spinal needle 22 has the preferred side port openings 29, spinal needle hub 30 preferably includes an indication 51 of the radial orientation of side port openings 29 to allow the practitioner to position the spinal needle in a preselected orientation.

Spinal needle 22 may also include a stylet 25 sized to fit within and substantially occlude hollow passage 24. Stylet 25, when used, serves to stiffen spinal needle 22 and to substantially prevent tissue from being forced into hollow passage 24. Alternatively, stylet 25 may be sized to occlude hollow bore 14 of epidural needle 12. In this case, stylet 25 would be removed after insertion of epidural needle 12 into the epidural space and spinal needle 22 positioned at the preselected projection distance.

Figure 7:
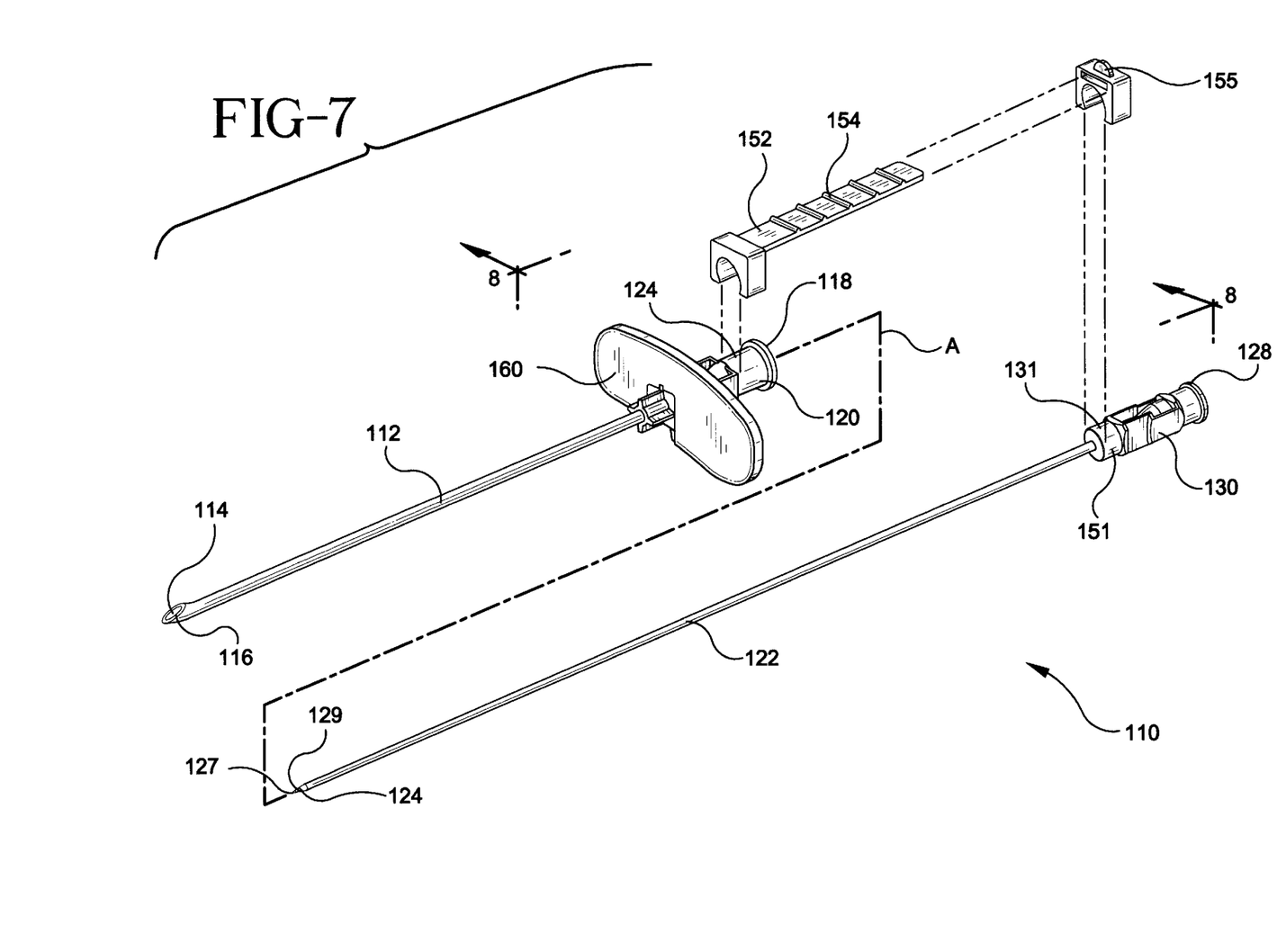
FIG. 7 is an exploded perspective view of an embodiment of the combined spinal epidural needle set of the invention.
Figure 8:
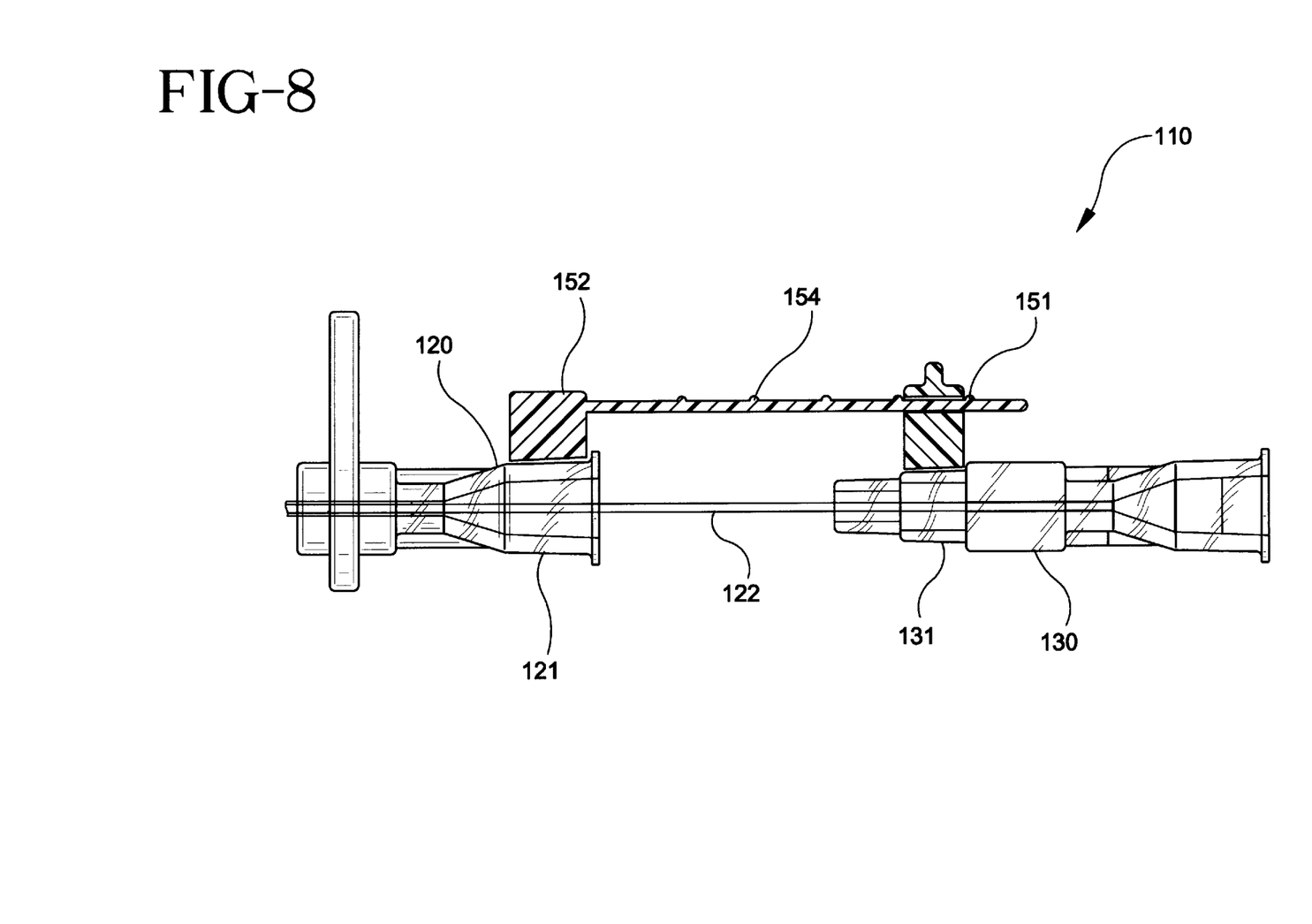
FIG. 8 is a cross-sectional view of the hub portion of the invention of FIG. 7 along the line 7—7.

Another embodiment of the present invention is illustrated in FIGS. 7 and 8. In this embodiment, the structure of the assembly is substantially similar to the embodiment of FIGS. 1–6. Accordingly, substantially similar components that perform substantially similar functions are numbered identically to those components of FIGS. 1–6 except that a "hundreds" prefix is used to identify those structures in FIGS. 7 and 8. Combined spinal epidural needle set 110 includes an epidural needle 112 with an overall length "l", a hollow bore 114 defining an axis A therethrough having an inside diameter "d". Needle 112 has an open distal end 116, a proximal end 118 and includes a hub 120. Needle set 110 includes a spinal needle 122 with an overall length "m" greater than length "l" of epidural needle 112. Spinal needle 122 has an outside diameter "e" less than said inside diameter "d" of bore 14 of epidural needle 112. Spinal needle 122 has a hollow passage 124 therethrough, a pointed distal end 126, preferably a "pencil point" 127, with at least one side port opening 129, a proximal end 128 and includes a hub 130. Analogous to the invention shown in FIGS. 1–6, spinal needle 122 is slidably disposed for movement within bore 114 of epidural needle 112 between a position where distal point 126 of the spinal needle is substantially coincident with open distal end 116 of epidural needle 112 and at least one position wherein distal point 126 of the spinal needle projects a distance "x" beyond open distal end 116 of epidural needle 112. In this embodiment, hubs 120 and 130, respectively, each include a receptacle portion 121 and 131, respectively, to receive a spacer fixture 152 with at least one stop 154 and a conjugate receiver 155 to receive spacer fixture 152 and releasably engage stop 154 to allow a practitioner to preselect the projection distance "x" of distal point 126 of the spinal needle with respect to open distal end 116 of the epidural needle. Preferably, spacer fixture 152 has a plurality of stops 154 to allow variable projection distance preselection between about point 126 being substantially coincident with open distal end 116 to point 126 having a projection distance about 18 mm. Preferably, spacer fixture 152 includes an elongate projection on hub of epidural needle 112 disposed to fit within receiver 155 and engage spacer fixture 152 thereby releasably fixing the position of spinal needle 122 with respect to the epidural needle 112. The plurality of stops 154 or space fixture itself 152 may serve as indication 151 of projection distance "x" of distal point 126 of the spinal needle.

Figure 9:
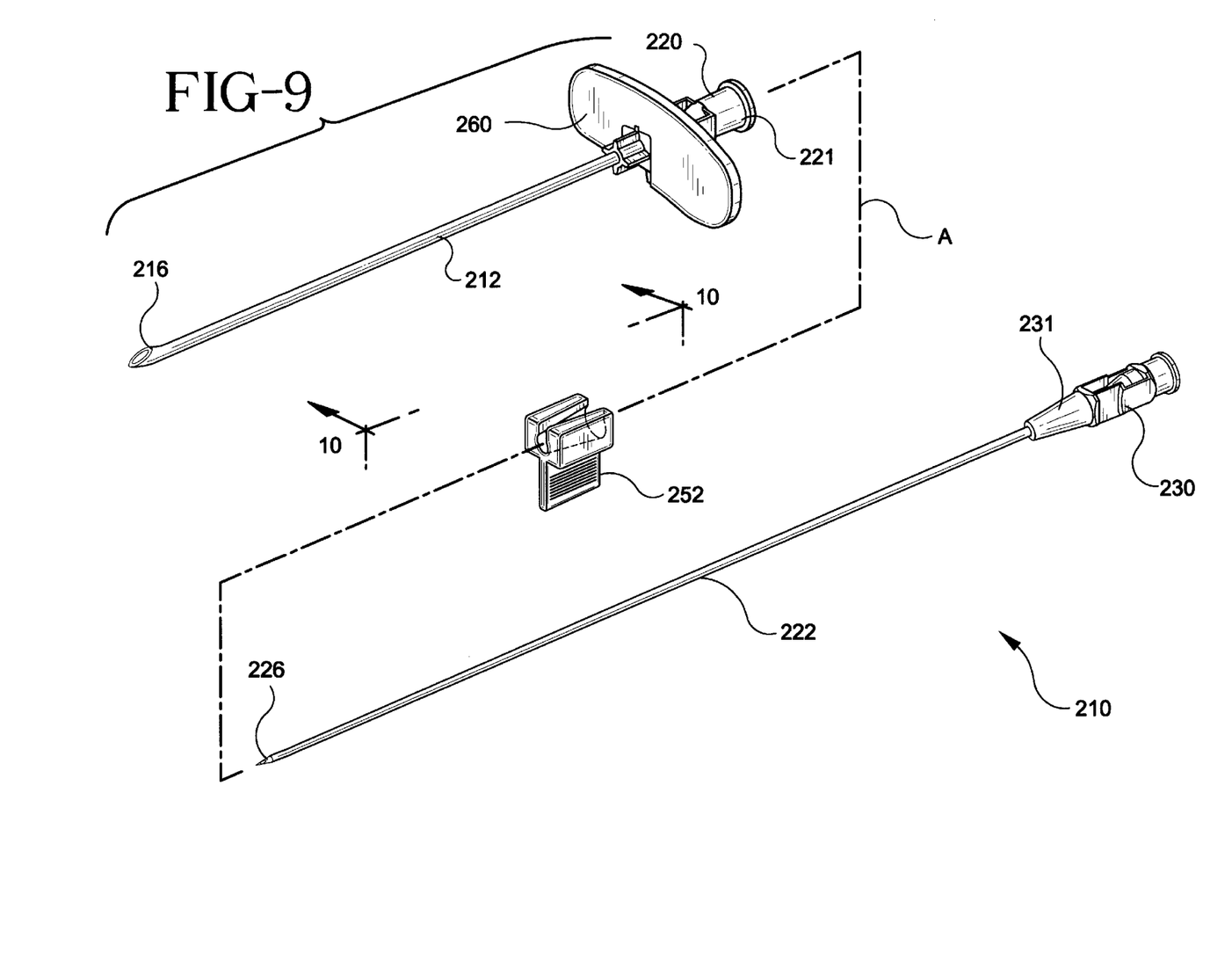
FIG. 9 is an exploded perspective view of another embodiment of the combined spinal epidural needle set of the invention.
Figure 10:
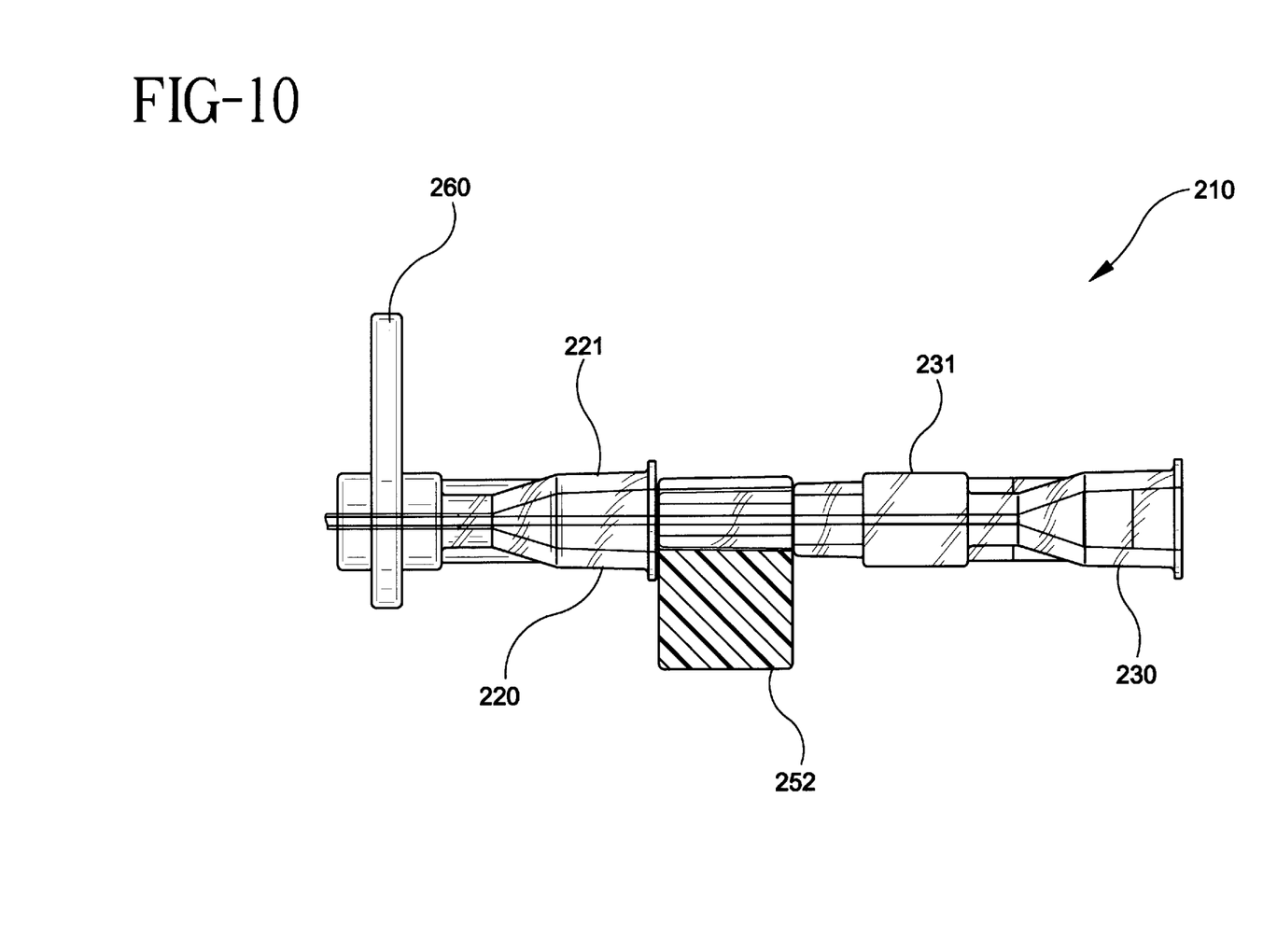
FIG. 10 is a partial cross-sectional view of the hub portion of the needle set of FIG. 9 taken along the line 10—10.

Another embodiment of the present invention is illustrated in FIGS. 9 and 10. In this embodiment, the structure of the assembly again is substantially similar to the embodiment of FIGS. 1–6. Accordingly, substantially similar components that perform substantially similar functions are numbered identically to those components of FIGS. 1–6 except that a "two hundreds" prefix is used to identify those structures in FIGS. 9 and 10. In this embodiment, a spacer fixture 252 is a unitary structure that releasably engages both receptacle portions 221 and 231 on hub 220 of epidural needle 212 and hub 230 of spinal needle 222 respectively. Distal point 226 being substantially coincident with open distal end 216 when spacer 252 is positioned on receptacle portions 221 and 231, respectively, of both of hubs 220 and 230. Distal point 226 of the spinal needle being movable to project beyond open distal end 216 of epidural needle 212 when spacer 252 is removed and hub 230 of spinal needle 222 is moved to engage hub 220 of epidural needle 212.

Figure 11:
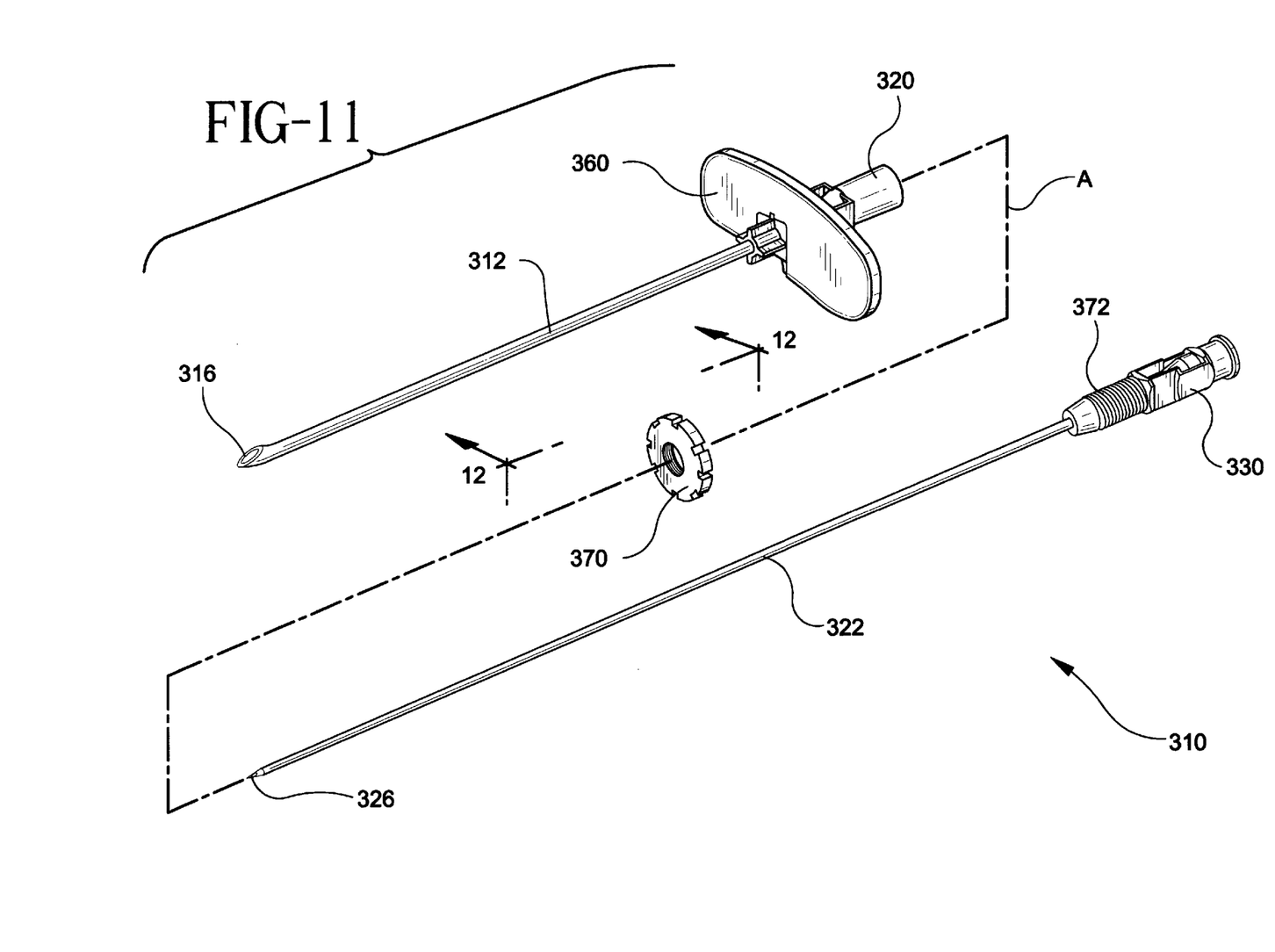
FIG. 11 is an exploded perspective view of yet another embodiment of the combined spinal epidural needle set of the invention.
Figure 12:
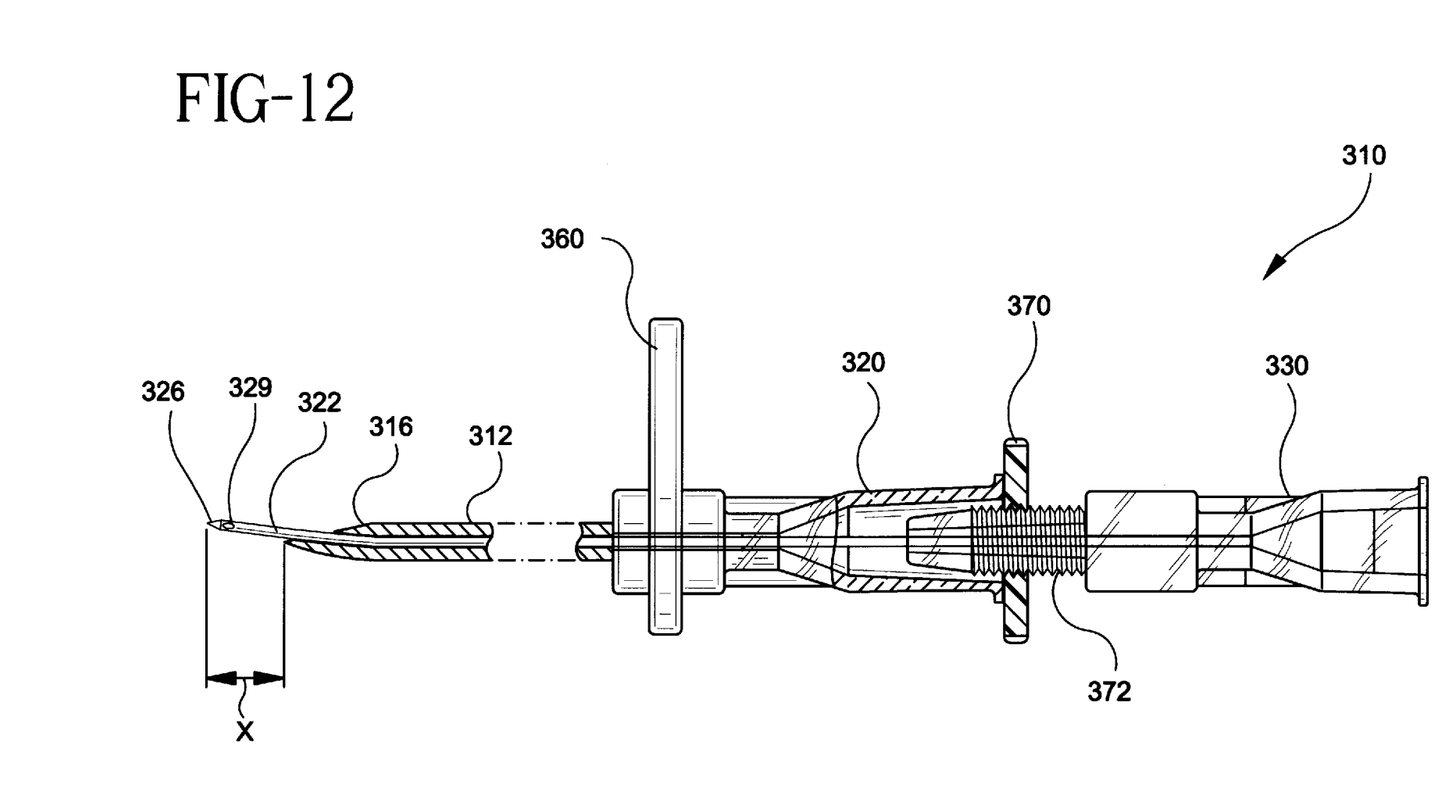
FIG. 12 is a partial cross-sectional view of the invention of FIG. 11 along the line 12—12 with the spinal needle partially extended.
Figure 13:
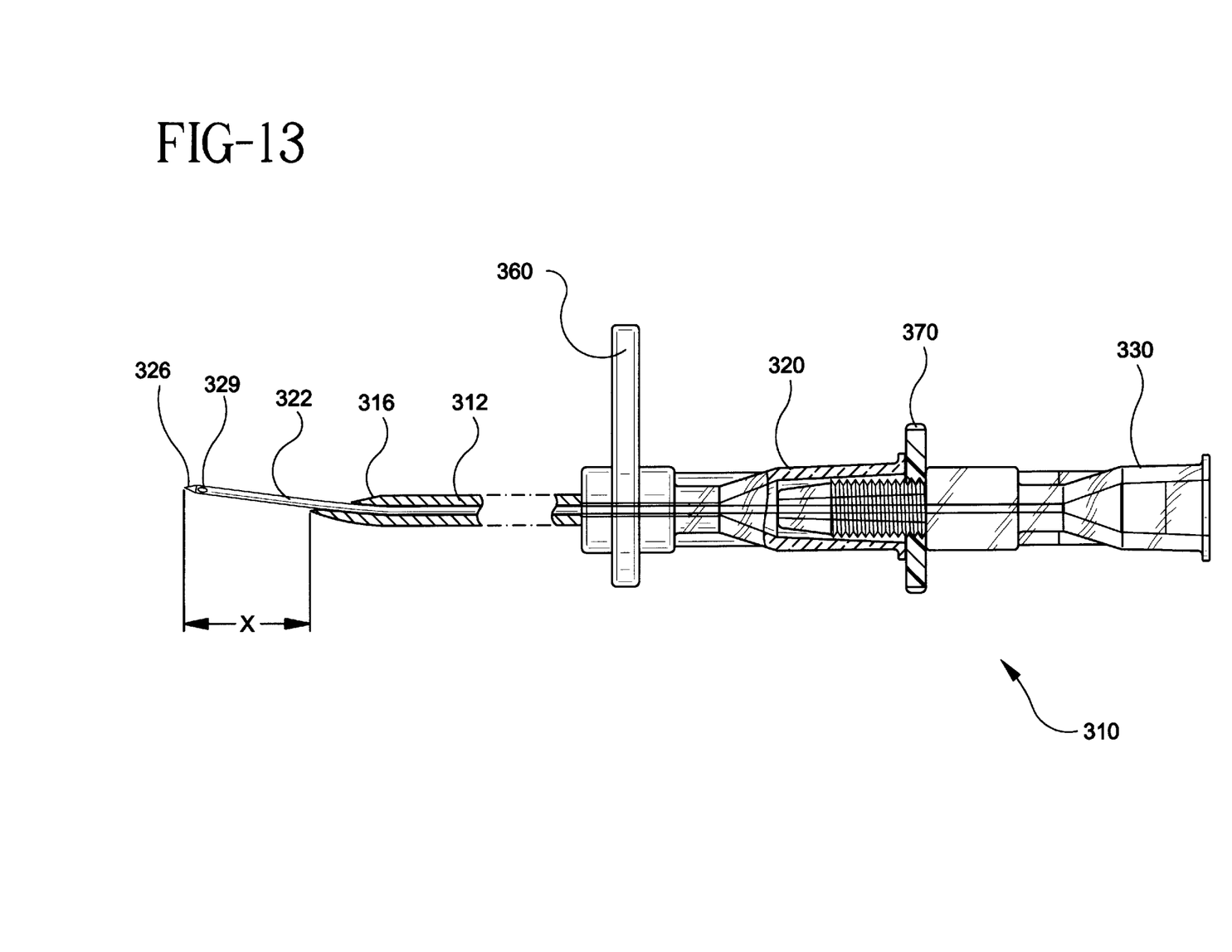
FIG. 13 is a partial cross-sectional view of the invention of FIG. 11 analogous to FIG. 12 with the spinal needle fully extended.

Yet another embodiment of the present invention is illustrated in FIGS. 11, 12 and 13. In this embodiment, the structure of the assembly again is substantially similar to the embodiment of FIGS. 1–6. Accordingly, substantially similar components that perform substantially similar functions are numbered identically to those components of FIGS. 1–6 except that a "three hundreds" prefix is used to identify those structures in FIGS. 11, 12 and 13. As shown in FIG. 11, the projection distance "x" of spinal needle point 326 with respect to open distal end 316 of the epidural needle is by rotation of a threaded washer 370 disposed on an elongate threaded portion 372 on spinal needle hub 330. Elongate threaded portion 372 is sized to fit within epidural needle hub 320, with the position of the distal point of the spinal needle with respect to the open distal end of the epidural needle being adjusted by rotation of threaded washer 370 about threaded portion 372.

Table of Hypodermic Tubing Nominal Sizes

| Gauge | Outside Diameter (mm) | Inside Diameter (mm) |
|---|---|---|
| 30 | 0.30 | 0.18 |
| 29 | 0.33 | 0.20 |
| 28 | 0.36 | 0.20 |
| 27 | 0.40 | 0.25 |
| 26 | 0.46 | 0.30 |
| 25 | 0.51 | 0.30 |
| 24 | 0.56 | 0.36 |
| 23 | 0.64 | 0.38 |
| 22 | 0.71 | 0.46 |
| 21 | 0.82 | 0.56 |
| 20 | 0.90 | 0.65 |
| 19 | 1.08 | 0.80 |
| 18 | 1.27 | 0.96 |
| 17 | 1.50 | 1.17 |
| 16 | 1.65 | 1.32 |

Referring to the table of nominal needle gauge sizes above, the preferred needle set of the invention includes a 25 gauge spinal needle slidably fit within a 17 gauge epidural needle. Alternatively, a combination of a 27 gauge spinal needle and an 18 gauge epidural needle, a 27 gauge spinal needle and a 17 gauge epidural needle or a 29 gauge spinal needle and an 18 gauge epidural needle or other combinations may be preferred for particular applications and are considered within the scope of the invention. The larger number gauge size (smaller outside diameters) combinations are often preferred for patients of smaller stature or for pediatric applications. Spinal needles having gauge sizes between about 22 gauge and 29 gauge are preferred by most practitioners for most applications Useful needle length ranges accommodative of most patient statures include epidural needle 12 having a length between about 8 cm to about 9 cm and spinal needle 22 having a length between about 14.5 cm to about 15.5 cm. For particular applications other lengths of both the spinal and epidural needles may be preferred. In general, consideration of a number of factors including, but not limited to, the desired spinal needle projection range and the patient stature range should be considered when selecting design parameters including, but not limited to, gauge sizes, needle lengths and the particular configuration of the projection adjustment mechanism for the invention. Numerous other combinations of these design parameters beyond those described in this disclosure may be envisioned and are considered to be within the scope of the invention.

Needle hubs 20 and 30 may be formed from thermoplastic materials including, but not limited to, polypropylene, polyethylene, polystyrene, polycarbonate and the like. Preferably, needle hubs 20 and 30 are formed from polypropylene or polypropylene. The cannula of epidural needle 12 and spinal needle 22 preferably are formed from stainless steel. Other components of the several embodiments of the assembly of the invention such as spacer 252 and threaded washer 370 may also be formed from thermoplastics similar to the hub materials. In all cases, since the assembly of the invention is almost always subjected to a sterilization process prior to use, consideration of the compatibility of the particular materials selected with each other and the sterilization conditions must be included in the selection process. Preferably, the shapes of needle hubs 20 and 30 includes gripping surfaces 23 to facilitate the practitioner's handling of the needle set.

Needle set 10 provides practitioners an improvement in their ability to deliver medicaments to the subarachnoid space. The needle set of the invention is easy to use and allows the practitioner more control of the penetration of the dura membrane than the currently available needle sets. By providing the practitioner with more control, the needle set of the invention substantially reduces the chance of adverse effects on the patient receiving the treatment.

What is claimed is:

1. A combined spinal epidural needle set comprising:
   an epidural needle with an overall length, a hollow bore defining an axis therethrough having an inside diameter, an open distal end and a proximal end including a hub;
   a spinal needle with an overall length greater than said epidural needle with an outside diameter less than said inside diameter of said bore of said epidural needle having a hollow passage therethrough, a pointed distal end, a proximal end including a hub, said spinal needle being slidably disposed for movement within said epidural needle between a position wherein said distal point of said spinal needle is substantially coincident with said open distal end of said epidural needle and at least one position wherein said distal point of said spinal needle projects a distance beyond said open distal end of said epidural needle; and
   wherein said both hubs of said epidural needle and said spinal needle each include adjustable engagement means for preselecting and releasably maintaining said position of said distal point of said spinal needle with respect to said open distal end of said epidural needle, and wherein said hub of said epidural needle engages said hub of said spinal needle when said distal point of said spinal needle projects beyond said distal point of said epidural needle.

2. The needle set of claim 1 wherein said engagement means comprises conjugate threads on said epidural needle hub and said spinal needle hub, said position of said distal point of said spinal needle with respect to said open distal end of said epidural needle being adjusted by rotation of said spinal needle with respect to said epidural needle, thereby advancing or retracting said distal point of said spinal needle.

3. The needle set of claim 2 wherein said hubs of said needles further include releasable means for substantially preventing unintentional movement of said spinal needle hub with respect to said epidural needle hub.

4. The needle set of claim 2 wherein said hub of said epidural needle comprises a female thread and said hub of said spinal needle comprises a male thread.

5. The needle set of claim 4 wherein said movement of said distal point of said spinal needle with respect to said open distal end of said epidural needle is a distance between about said position wherein said distal ends are substantially coincident to a position wherein said distal point of said spinal needle is projected about 18 mm.

6. The needle set of claim 1 wherein said adjustable engagement means comprises a receptacle portion on said hub of said epidural needle, a receptacle portion on said hub of said spinal needle, a spacer fixture having at least one stop fitted to one of said receptacle portions and a conjugate for said spacer fixture fitted to said other receptacle portion, said conjugate disposed to releasably engage said at least one stop for preselecting said position of distal point of said spinal needle with respect to said open distal end of said epidural needle.

7. The needle set of claim 6 wherein said spacer fixture is a unitary structure further comprising means for releasably engaging both said receptacle portion on said hub of said epidural needle and said receptacle portion on said hub of said spinal needle, said distal point of said epidural needle and wherein said distal point of said spinal needle being substantially coincident when said spacer is positioned on said receptacle portions of both of said hubs and said distal point of said spinal needle being movable to project beyond said open distal end of said epidural needle when said spacer is removed and said hub of said spinal needle is moved to engage said hub of said epidural needle.

8. The needle set of claim 1 wherein said adjustable engagement means further includes releasable gripping means on said hub of said spinal needle having a receiver therein and an elongate projection on said hub of said epidural needle disposed to fit within said receiver and engage said gripping means thereby releasably fixing said position of said spinal needle with respect to said epidural needle.

9. The needle set of claim 8 wherein said releasable gripping means on said hub is biased to normally engage said projection, said gripping means further including an outwardly projecting button disposed to allow an operator to apply a force to said gripping means to overcome said bias and allow movement of said spinal needle with respect to said epidural needle.

10. The needle set of claim 1 wherein said adjustable engagement means further comprises an elongate threaded portion on said hub of said spinal needle and a conjugate threaded washer disposed thereon to engage said hub of said epidural needle, said position of said distal point of said spinal needle with respect to said open distal end of said epidural needle being adjusted by rotation of said washer about said threaded portion.

11. The needle set of claim 1 further comprising a removable stylet disposed within said spinal needle to substantially occlude said passage.

12. The needle set of claim 1 wherein said distal point configuration of said epidural needle is selected from the group consisting of a modified Touhy configuration having a beveled surface at about 45 degrees terminating at said axis of said bore and a Crawford configuration having a beveled surface at about 45 degrees to said axis across said bore of said needle.

13. The needle set of claim 1 wherein said spinal needle further comprises a sidewall having a closed distal point with at least one opening in said sidewall into said passage adjacent to said distal point.

14. The needle set of claim 13 wherein said point of said spinal needle comprises a pencil point, said spinal needle having two substantially diametrically opposed openings in said sidewall each having a center being located between about 2 mm to about 3 mm proximal to said pencil point.

15. The needle set of claim 14 wherein said proximal hub of said spinal needle comprises an indicia of an alignment of said opposed openings.

16. The needle set of claim 15 wherein said proximal hub of said spinal needle further comprises a female luer fitting.

17. The needle set of claim 1 wherein said adjustable engagement means further comprises indicator means for indicating said projection of said distal point of said spinal needle with respect to said open distal end of said epidural needle.

18. The needle set of claim 1 wherein said proximal hub of said epidural needle further comprises a grip to facilitate placement of said epidural needle into a patient.

19. The needle set of claim 1 wherein said epidural needle and said spinal needle are selected from the group consisting of a 25 gauge spinal needle and a 17 gauge epidural needle, a 27 gauge spinal needle and an 18 gauge epidural needle, a 27 gauge spinal needle and a 17 gauge epidural needle and a 29 gauge spinal needle and an 18 gauge epidural needle.

20. A combined spinal epidural needle set comprising:

an epidural needle with an overall length, a hollow bore defining an axis therethrough having an inside diameter, an open distal end and a proximal end including a hub comprising a female luer fitting;

a spinal needle with an overall length greater than said epidural needle with an outside diameter less than said inside diameter of said bore of said epidural needle having a hollow passage therethrough, a pointed distal end, a proximal end including a hub comprising a male luer, said spinal needle being slidably disposed for movement within said epidural needle between a position wherein said distal point of said spinal needle is substantially coincident with said open distal end of said epidural needle and at least one position wherein said distal point of said spinal needle projects a distance beyond said open distal end of said epidural needle, and wherein said male luer fitting on said spinal needle hub is disposed to engage said female luer fitting on said proximal hub of said epidural needle when said spinal needle distal point is projected beyond said open distal end of said epidural needle; and wherein said both hubs of said epidural needle and said spinal needle each include adjustable engagement means for preselecting and releasably maintaining said position of said distal point of said spinal needle with respect to said open distal end of said epidural needle.

* * * * *